United States Patent
Lachaine

(10) Patent No.: US 10,525,284 B2
(45) Date of Patent: Jan. 7, 2020

(54) MOTION MANAGEMENT IN IMAGE-GUIDED RADIOTHERAPY

(71) Applicant: Elekta LTD., Montreal (CA)

(72) Inventor: Martin Emile Lachaine, Montreal (CA)

(73) Assignee: Elekta LTD, Montreal, Quebec (CA)

(*) Notice: Subject to any disclaimer, the term of this patent is extended or adjusted under 35 U.S.C. 154(b) by 0 days.

(21) Appl. No.: 16/075,125

(22) PCT Filed: Oct. 21, 2016

(86) PCT No.: PCT/IB2016/001613
§ 371 (c)(1),
(2) Date: Aug. 2, 2018

(87) PCT Pub. No.: WO2017/137795
PCT Pub. Date: Aug. 17, 2017

(65) Prior Publication Data
US 2019/0038919 A1 Feb. 7, 2019

Related U.S. Application Data

(60) Provisional application No. 62/292,726, filed on Feb. 8, 2016.

(51) Int. Cl.
*A61N 5/10* (2006.01)
*G06T 11/00* (2006.01)
(Continued)

(52) U.S. Cl.
CPC ............ *A61N 5/1049* (2013.01); *A61N 5/107* (2013.01); *A61N 5/1039* (2013.01);
(Continued)

(58) Field of Classification Search
CPC .. A61N 5/1049; A61N 5/1039; A61N 5/1045; A61N 5/1064; A61N 5/1067;
(Continued)

(56) References Cited

U.S. PATENT DOCUMENTS 9,974,977 B2 * 5/2018 Lachaine ............... G06T 7/11
2008/0021300 A1 1/2008 Allison
(Continued)

FOREIGN PATENT DOCUMENTS

CN 109219469 A 1/2019
JP 2008080131 A 4/2008
(Continued)

OTHER PUBLICATIONS

"Australian Application Serial No. 2016392399, First Examination Report dated Feb. 6, 2019", 2 pgs.
(Continued)

*Primary Examiner* — Nicole M Ippolito
(74) *Attorney, Agent, or Firm* — Schwegman Lundberg & Woessner, P.A.; Sanjay Agrawal

(57) ABSTRACT

Systems and methods for managing motions of an anatomical region of interest of a patient during image-guided radiotherapy are disclosed. An exemplary system may include an image acquisition device, a radiotherapy device, and a processor device. The processor device may be configured to determine a primary plane of motion of the anatomical region of interest and determine a plurality of 2D slices parallel to the primary plane. The plurality of 2D slices may define a 3D volume substantially enclosing the anatomical region of interest. The processor device may also be configured to control the image acquisition device to acquire a plurality of 2D images based on the plurality of 2D slices and determine a motion of the anatomical region of interest based on at least a subset of the acquired plurality of 2D images. The processor device may be further configured to control radiation delivery based on the determined motion.

34 Claims, 9 Drawing Sheets

(51) Int. Cl.
*G06T 7/246* (2017.01)
*G01R 33/48* (2006.01)
*G06T 7/254* (2017.01)

(52) U.S. Cl.
CPC ......... *A61N 5/1045* (2013.01); *A61N 5/1064* (2013.01); *A61N 5/1067* (2013.01); *A61N 5/1068* (2013.01); *A61N 5/1077* (2013.01); *G01R 33/4808* (2013.01); *G06T 7/246* (2017.01); *G06T 7/254* (2017.01); *G06T 11/003* (2013.01); *A61N 2005/1055* (2013.01); *G06T 2207/10016* (2013.01); *G06T 2207/10076* (2013.01); *G06T 2207/10081* (2013.01); *G06T 2207/10088* (2013.01); *G06T 2207/30096* (2013.01)

(58) Field of Classification Search
CPC .... A61N 5/1068; A61N 5/107; A61N 5/1077; G06T 7/254; G06T 7/246; G06T 11/003; G01R 33/4808
USPC ........................................... 250/492.1, 492.3
See application file for complete search history.

(56) References Cited

U.S. PATENT DOCUMENTS

| | | | |
|---|---|---|---|
| 2008/0212737 | A1 | 9/2008 | D'souza et al. |
| 2010/0329414 | A1 | 12/2010 | Zhu |
| 2011/0172526 | A1 | 7/2011 | Lachaine et al. |
| 2015/0169836 | A1 | 6/2015 | Vahala et al. |
| 2018/0256064 | A1* | 9/2018 | Lachaine ............. A61N 5/1049 |

FOREIGN PATENT DOCUMENTS

| | | | |
|---|---|---|---|
| JP | 2012531222 | A | 12/2012 |
| JP | 2015500053 | A | 1/2015 |
| WO | 2016094284 | | 6/2016 |
| WO | WO-2016094284 | A9 | 6/2016 |
| WO | 2017137795 | | 8/2017 |

OTHER PUBLICATIONS

"European Application Serial No. 16889726.2, Extended European Search Report dated Jan. 30, 2019", 5 pgs.

"International Application Serial No. PCT/IB2016/001613, International Search Report dated Jan. 31, 2017", (Jan. 31, 2017), 3 pgs.

"International Application Serial No. PCT/IB2016/001613, Written Opinion dated Jan. 31, 2017", (Jul. 31, 2017), 4 pgs.

"International Application Serial No. PCT IB2016 001613, International Preliminary Report on Patentability dated Aug. 23, 2018", 6 pgs.

"European Application Serial No. 16889726.2, Response filed Jul. 31, 2019 to Extended European Search Report dated Jan. 30, 2019", 28 pgs.

"Japanese Application Serial No. 2018-560263, Notification of Reasons for Rejection dated Jun. 18, 2019", w/ English Translation, 8 pgs.

* cited by examiner

2D Image Acquisition

MOTION MANAGEMENT IN IMAGE-GUIDED RADIOTHERAPY

CROSS-REFERENCE TO RELATED APPLICATION

The present application is a U.S. National Stage Filing under 35 U.S.C. 371 from International Application No. PCT/IB2016/001613, filed on Oct. 21, 2016, and published as WO2017/137795 on Aug. 17, 2017, which claims the benefit of priority to U.S. Provisional Application No. 62/292,726, filed on Feb. 8, 2016; the benefit of priority of each of which is hereby claimed herein, and which applications and publication are hereby incorporated herein by reference in their entirety.

TECHNICAL FIELD

This disclosure relates generally to radiation therapy or radiotherapy. More specifically, this disclosure relates to systems and methods for managing patient motions in image-guided radiotherapy.

BACKGROUND

Radiotherapy is used to treat cancers and other ailments in mammalian (e.g., human and animal) tissue. An exemplary radiotherapy is provided using a linear accelerator (LINAC), whereby a tumor is irradiated by high-energy particles (e.g., electrons, protons, ions and the like). During the course of radiation treatment, images of the tumor and surround tissues may be acquired using an image acquisition device to improve the accuracy of radiation field placement. For example, information revealed by the images may be used to compensate for changes of the tumor due to treatment or due to movement of the patient.

Images may be acquired prior to a treatment session to determine changes of the tumor between sessions, or during a treatment session to determine changes of the tumor due to, for example, movements of the patient. Magnetic Resonance Imaging (MRI) techniques may be used to produce such images thanks to its excellent soft tissue contract and high resolution. However, the acquisition time of MRI images, especially three-dimensional (3D) MRI images, is relatively long. For example, a 3D MRI image may take several minutes to acquire. Such a long acquisition time makes 3D MRI unsuitable for tracking movement related tumor changes during a treatment session.

SUMMARY

Certain embodiments of the present disclosure relate to a radiotherapy system. The radiotherapy system may include an image acquisition device configured to acquire images of an anatomical region of interest of a patient. The radiotherapy system may also include a radiotherapy device configured to deliver a dose of radiation to the anatomical region of interest based on the images of the anatomical region of interest. The radiotherapy system may further include a processor device. The processor device may be configured to determine a primary plane of motion of the anatomical region of interest. The processor device may also be configured to determine a plurality of 2D slices parallel to the primary plane. The plurality of 2D slices may define a 3D volume substantially enclosing the anatomical region of interest. The processor device may also be configured to control the image acquisition device to acquire a plurality of 2D images based on the plurality of 2D slices. The processor device may also be configured to determine a motion of the anatomical region of interest based on at least a subset of the acquired plurality of 2D images. In addition, the processor device may be configured to control radiation delivery based on the determined motion.

Certain embodiments of the present disclosure relate to a method for managing motions of an anatomical region of interest of a patient during an image-guided radiotherapy session. The method may be implemented by a processor device of a radiotherapy system. The method may include determining a primary plane of motion of the anatomical region of interest. The method may also include determining a plurality of 2D slices parallel to the primary plane. The plurality of 2D slices may define a three-dimensional (3D) volume substantially enclosing the anatomical region of interest. The method may also include controlling an image acquisition device to acquire a plurality of 2D images based on the plurality of 2D slices. The method may also include determining a motion of the anatomical region of interest based on at least a subset of the acquired plurality of 2D images. In addition, the method may include controlling a radiotherapy device to deliver radiation based on the determined motion.

Certain embodiments of the present disclosure relate to a radiotherapy system. The radiotherapy system may include an image acquisition device configured to acquire MRI images of an anatomical region of interest of a patient. The radiotherapy system may also include a radiotherapy device including a linear accelerator (LINAC) and configured to deliver a dose of radiation to the anatomical region of interest based on the images of the anatomical region of interest. The radiotherapy system may further include a processor device. The processor device may be configured to determine a primary plane of motion of the anatomical region of interest. The primary plane of motion may include a sagittal plane, a coronal plane, or a transverse plane. The processor device may also be configured to determine a plurality of 2D slices parallel to the primary plane. The plurality of 2D slices may define a 3D volume substantially enclosing the anatomical region of interest. The plurality of 2D slices may also define a plurality of spatial locations relative to the anatomical region of interest. The processor device may also be configured to control the image acquisition device to acquire a series of 2D images by repeatedly sweeping across the plurality of 2D slices. Each 2D image within the series may correspond to one of the plurality of 2D slices. The processor device may also be configured to construct a four-dimensional (4D) image of the 3D volume based on at least a subset of the series of 2D images. The processor device may be configured to receive a first 2D image within the series that corresponds to a first 2D slice; insert the first 2D image into the 4D image; receive a second 2D image within the series that also corresponds to the first 2D slice; and replace the first 2D image in the 4D image with the second 2D image. The processor device may also be configured to determine a motion of the anatomical region of interest based on a comparison between 3D snapshots of the 4D image at different times during a radiotherapy session. The motion of the anatomical region of interest may include at least one of position change or deformation. In addition, the processor device may be configured to control radiation delivery based on the determined motion, including at least one of control a gating of a radiation beam; control a modification of a multi-leaf collimator (MLC); or control a movement of a patient supporting system.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

The foregoing general description and the following detailed description are exemplary and explanatory only, and are not restrictive.

BRIEF DESCRIPTION OF THE DRAWINGS

The accompanying drawings, which constitute a part of this specification, illustrate several embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. And the singular forms "a," "an," and "the" are intended to include plural references, unless the context clearly dictates otherwise.

Systems and methods consistent with the present disclosure are directed to image-guided radiation therapy or radiotherapy (IGRT). As used herein, the terms "radiation therapy," "radiotherapy," and "radiation oncology" are used interchangeably. IGRT refers to a technique of using frequent 2D or 3D imaging to direct radiotherapy during a course of radiation treatment. IGRT technique may be used to improve the accuracy of radiation field placement, and to reduce the exposure of healthy tissue during radiation treatments.

Figure 1:
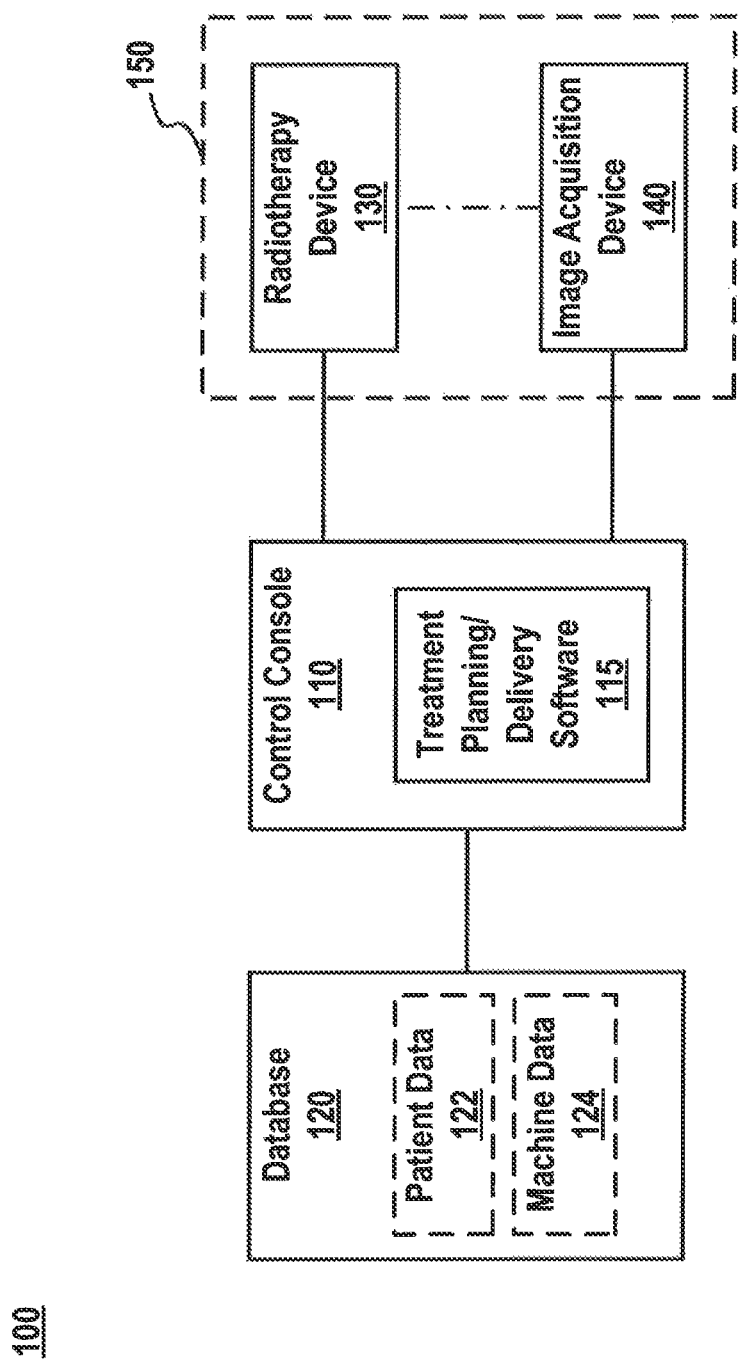
FIG. 1 illustrates an exemplary radiotherapy system, according to some embodiments of the present disclosure.

FIG. 1 illustrates an exemplary radiotherapy system 100, according to some embodiments of the present disclosure. Radiotherapy system 100 may be an IGRT system. As shown in FIG. 1, radiotherapy system 100 may include a control console 110, a database 120, a radiotherapy device 130, and an image acquisition device 140. In some embodiments, radiotherapy device 130 and image acquisition device 140 may be integrated into a single image-guided radiotherapy device 150, as indicated by the dashed box 150 in FIG. 1. In some embodiments, radiotherapy device 130 and image acquisition device 140 may be separate devices. In some embodiments, radiotherapy device 130 and image acquisition device 140 may be physically or communicative connected to each other, as indicated by a dotted-dashed line between radiotherapy device 130 and image acquisition device 140 in FIG. 1.

Control console 110 may include hardware and software components to control radiotherapy device 130 and image acquisition device 140 and/or to perform functions or operations such as treatment planning, treatment execution, image acquisition, image processing, motion tracking, motion management, or other tasks involved in a radiotherapy process. The hardware components may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. The software components may include operation system software, application software, etc. For example, as shown in FIG. 1, control console 110 may include treatment planning/delivery software 115 that may be stored in a memory/storage device of control console 110. Software 115 may include computer readable and executable codes or instructions. A processor device of control console 110 may be communicatively connected to the memory/storage device storing software 115 to access and execute the codes or instructions. The execution of the codes or instructions may cause the processor device to perform operations to achieve one or more functions consistent with the disclosed embodiments.

Control console 110 may be communicatively connected to database 120 to access data. In some embodiments, database 120 may be implemented using local hardware devices, such as one or more hard drives, optical disks, and/or servers that are in the proximity of control console 110. In some embodiments, database 120 may be implemented in a data center or a server located remotely with respect to control console 110. Control console 110 may access data stored in database 120 through wired or wireless communication.

Database 120 may include patient data 122. Patient data may include information such as imaging data associated with a patient (e.g., MRI, CT, X-ray, PET, SPECT, and the like); anatomical region, organ, or volume of interest segmentation data; functional organ modeling data (e.g., serial versus parallel organs, and appropriate dose response models); radiation dosage data (e.g., may include dose-volume histogram (DVH) information); lab data (e.g., hemoglobin, platelets, cholesterol, triglycerides, creatinine, sodium, glucose, calcium, weight); vital signs (blood pressure, temperature, respiratory rate and the like); genomic data (e.g., genetic profiling); demographics (age, sex, ethnicity, etc.); other diseases affecting the patient (e.g., cardiovascular disease, respiratory disease, diabetes, radiation hypersensitivity syndromes, and the like); medications and drug reactions; diet and lifestyle (e.g., smoking or non-smoking); environmental risk factors; tumor characteristics (histological type, tumor grade, hormone and other receptor status, tumor size, vascularity cell type, cancer staging, Gleason score, etc.); previous treatments (e.g., surgeries, radiation, chemotherapy, hormone therapy, etc.); lymph node and distant metastases status; genetic/protein biomarkers (e.g., MYC, GADD45A, PPM1D, BBC3, CDKN1A, PLK3, XPC, AKT1, RELA, BCL2L1, PTEN, CDK1, XIAP, and the like); single nucleotide polymorphisms (SNP) analysis (e.g., XRCC1, XRCC3, APEX1, MDM2, TNFR, MTHFR, MTRR, VEGF, TGFβ, TNFα, etc.), and the like.

Database 120 may include machine data 124. Machine data 124 may information associated with radiotherapy device 130, image acquisition device 140, or other machines relevant to radiotherapy, such as radiation beam size, arc placement, on/off time duration, coordinate system, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Radiotherapy device 130 may include a Leksell Gamma Knife, a LINAC, or other suitable devices capable of delivering radiation to an anatomical region of interest of a patient in a controllable manner.

Figure 2:
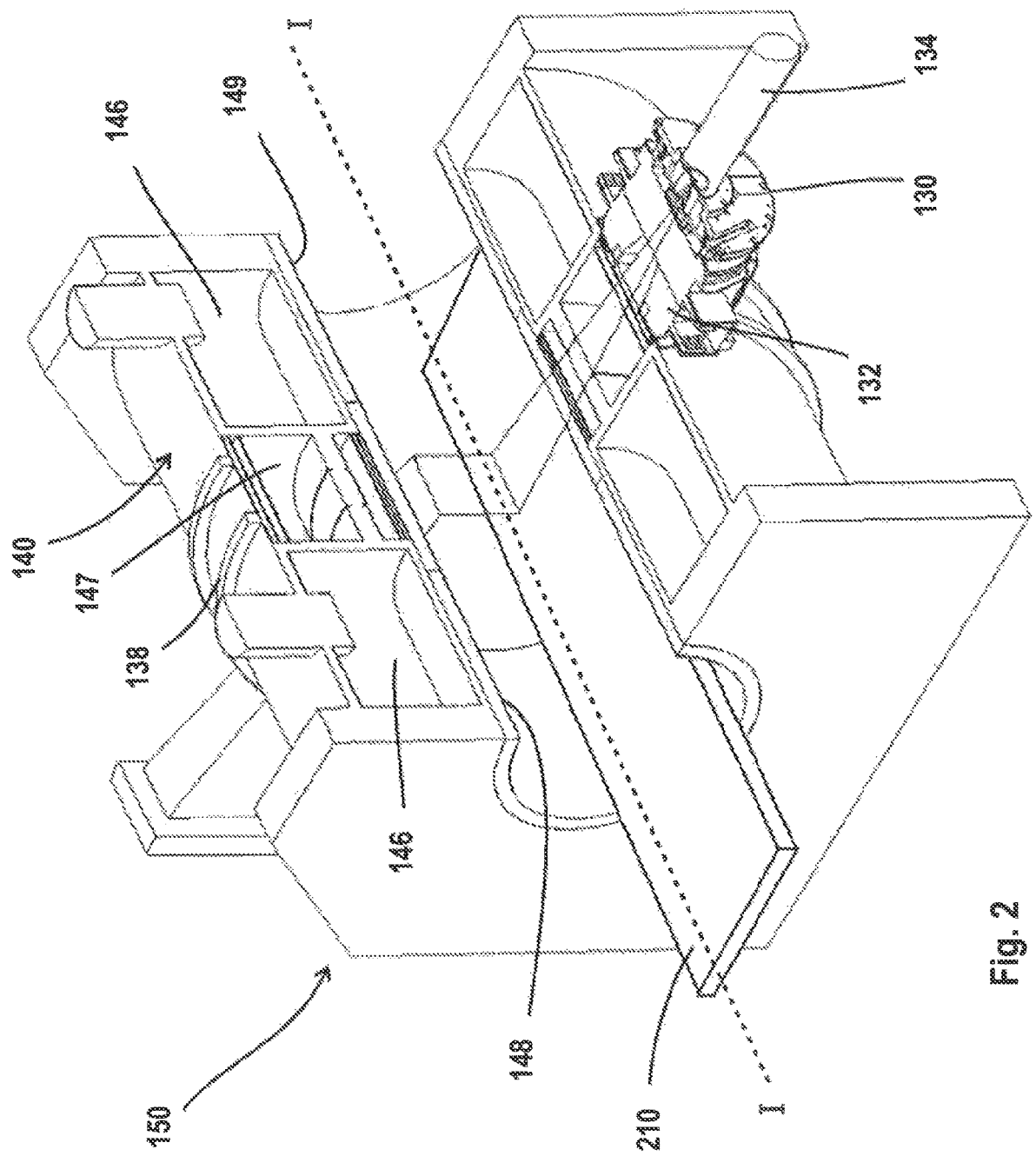
FIG. 2 illustrates an exemplary image-guided radiotherapy device, according to some embodiments of the present disclosure.

FIG. 2 illustrates an exemplary image-guided radiotherapy device 150, according to some embodiments of the present disclosure. Device 150 includes a couch 210, an image acquisition portion corresponding to image acquisition device 140, and a radiation delivery portion corresponding to radiotherapy device 130.

Couch 210 may be used for supporting a patient (not shown) during a treatment session, and may also be referred to as a patient supporting system. Couch 210 may be movable along a horizontal, translation axis (labelled "I"), such that the patient resting on couch 210 can be moved into and/or out of device 150. In some embodiments, couch 210 may be rotatable around a central vertical axis of rotation, transverse to the translation axis. Couch 210 may be motorized to move in various directions and rotate along various axes to properly position the patient according to a treatment plan.

Image acquisition device 140 may include an MRI machine used to acquire 2D or 3D MRI images of a patient before, during, and/or after a treatment session. Image acquisition device 140 may include a magnet 146 for generating a primary magnetic field for magnetic resonance imaging. The magnetic field lines generated by operation of magnet 146 may run substantially parallel to the central translation axis I. Magnet 146 may include one or more coils with an axis that runs parallel to the translation axis I. In some embodiments, the one or more coils in magnet 146 may be spaced such that a central window 147 of magnet 146 is free of coils. In other embodiments, the coils in magnet 146 may be thin enough or of a reduced density such that they are substantially transparent to radiation of the wavelength generated by radiotherapy device 130. Image acquisition device 140 may also include one or more active shielding coils, which may generate a magnetic field outside magnet 146 of approximately equal magnitude and opposite polarity to cancel the magnetic field outside magnet 146. A radiation source 134 of radiotherapy device 130 may be positioned in the region where the magnetic field is cancelled, at least to a first order.

Image acquisition device 140 may also include two gradient coils 148 and 149, which may generate a gradient magnetic field that is superposed on the primary magnetic field. Coils 148 and 149 may generate a gradient in the resultant magnetic field that allows spatial encoding of the protons so that their position can be determined. Gradient coils 148 and 149 may be positioned around a common central axis with the magnet 146, and may be displaced from on another along that central axis. The displacement may create a gap, or window, between coils 148 and 149. In the embodiments wherein magnet 146 also includes a central window 147 between coils, the two windows may be aligned with each other.

Radiotherapy device 130 may include the source of radiation 134, such as an X-ray source or a linear accelerator, and a multi-leaf collimator (MLC) 132. Radiotherapy device 130 may be mounted on a chassis 138. Chassis 138 may be continuously rotatable around couch 210 when it is inserted into the treatment area, powered by one or more chassis motors. A radiation detector may also be mounted on chassis 138 if desired, preferably opposite to radiation source 134 and with the rotational axis of chassis 138 positioned between radiation source 134 and the detector. The control circuitry of radiotherapy device 130 may be integrated within device 150 or remote from it, and is functionally represented by control console 110 of FIG. 1.

During a radiotherapy treatment session, a patient may be positioned on couch 210, which may be inserted into the treatment area defined by magnetic coils 146, 148, 149, and chassis 138. Control console 110 may control radiation source 134, MLC 132, and the chassis motor(s) to deliver radiation to the patient through the window between coils 148 and 149.

Figure 3:
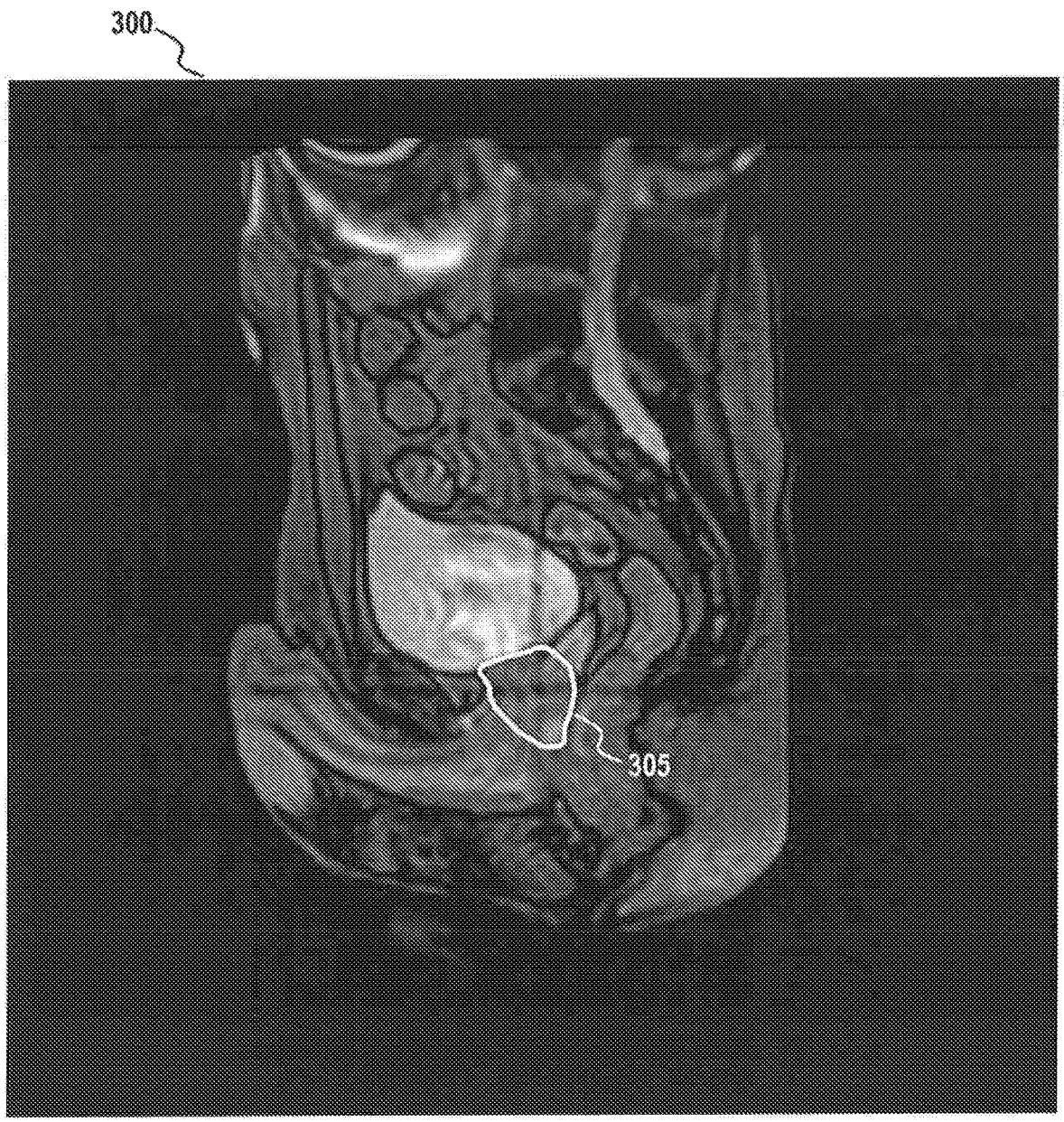
FIG. 3 is an exemplary image showing an exemplary anatomical region of interest, according to some embodiments of the present disclosure.

FIG. 3 is an exemplary image 300 showing an exemplary anatomical region of interest, according to some embodiments of the present disclosure. As used herein, an anatomical region of interest may include an organ, an organ at risk (OAR), a tumor, a surrounding tissue, a radiotherapy target, an isocenter, or any other anatomical structures relevant to radiotherapy. Image 300 is a 2D MRI image of a patient's lower abdominal area, parallel to a sagittal plane. As used herein, a sagittal plane is a plane parallel to the sagittal suture, dividing a body into left and right portions; a coronal plane (also known as a frontal plane) divides the body into dorsal and ventral (back and front, or posterior and anterior) portions; a transverse plane divides the body into cranial and caudal (superior and inferior, or head and tail) portions. Image 300 includes an image of an anatomical region of interest—the prostate of the patient, indicated by contour 305. Contour 305 may be obtained using image registration and/or segmentation techniques. During a radiotherapy session, the position, size, and/or shape of the prostate may change. For example, the prostate may move, relatively slowly, due to, for example, relaxation or bladder filling. The prostate may occasionally undergo relatively fast movements due to, for example, gas or coughing. The shape/size of the prostate may also change due to deformation or reduction of cancerous cells. As used herein, a change in the position, shape, or size of an anatomical region of interest is commonly referred to a motion of the anatomical region of interest. In another example, the cervix may move in a manner similar to the prostate. The imaging techniques disclosed herein enable accurate capture of one or more motions of an anatomical region of interest during a radiation delivery session. The anatomical region of interest may include prostate, cervix, uterus, rectum, bladder, penile bulb, lumpectomy cavity in a breast, tumor, node, etc.

In some embodiments, the motions of an anatomical region of interest, such as a prostate, may be primarily in the posterior/anterior and superior/inferior directions, and the motions in the left/right directions may be insignificant. In such cases, the sagittal plane may be defined as a primary plane of motion. In some embodiments, such as when treating patients having prostate cancers, the primary plane of motion may be determined to be the same, e.g., the sagittal plane, for different patients. In some embodiments, such as when treating patients having liver cancers, the primary plane of motion may be patient dependent and may be determined based on images of the anatomical region of interest of individual patient.

Figure 4:
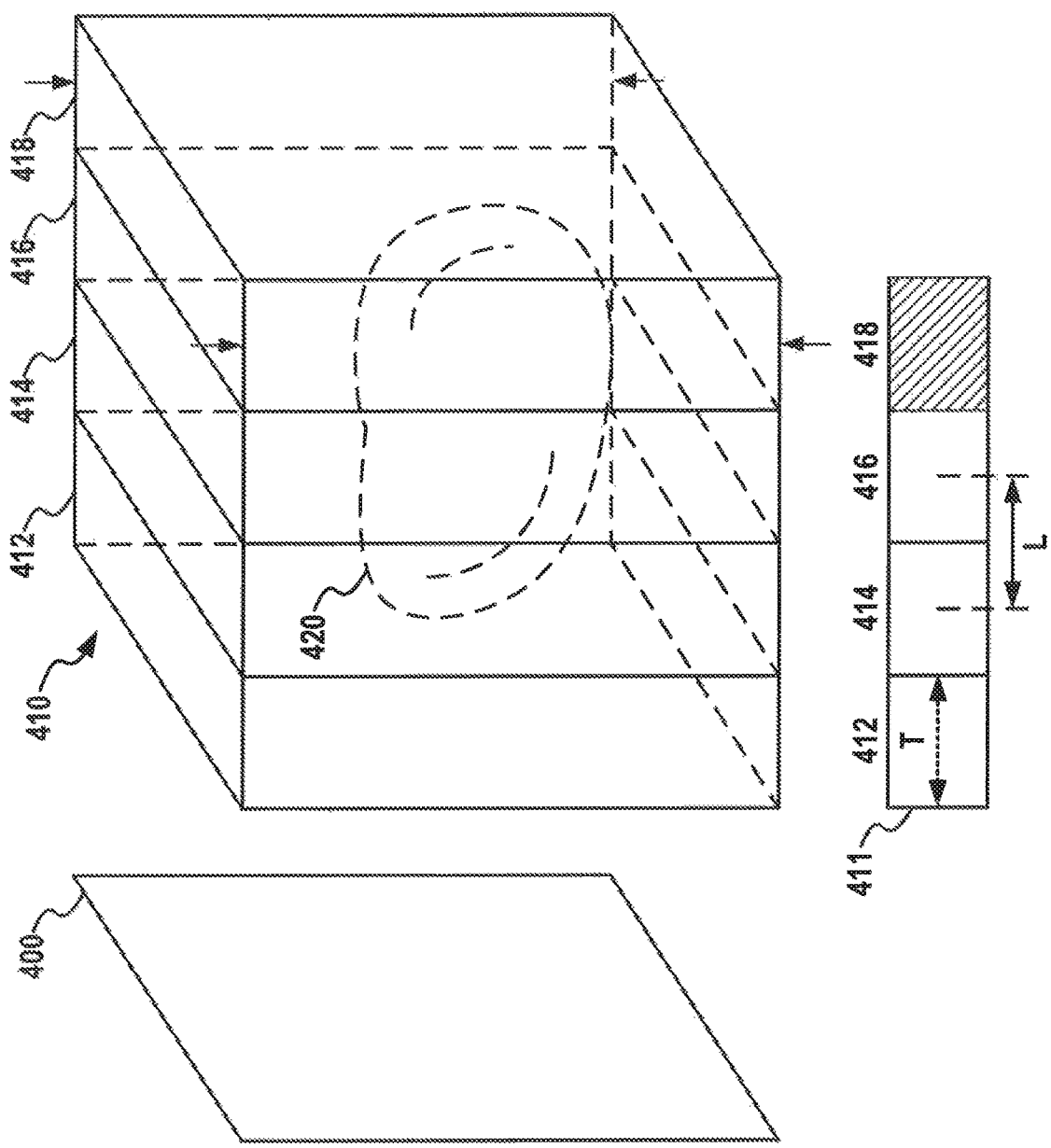
FIG. 4 illustrates an exemplary primary plane of motion and exemplary 2D slices, according to some embodiments of the present disclosure.

FIG. 4 illustrates an exemplary primary plane of motion 400 and exemplary 2D slices, according to some embodiments of the present disclosure. Referring to FIG. 4, primary plane of motion 400 may be determined by control console 110 based on, for example, the type of the anatomical region of interest, the treatment plan, the medical images of the anatomical region of interest, etc. For treating prostate cancer, for example, the sagittal plane may be determined to be the primary plane of motion 400. Control console 110 may then determine a plurality of 2D slices parallel to primary plane of motion 400, such as slices 412, 414, 416, and 418. The plurality of 2D slices may define a 3D volume 410 substantially enclose an anatomical region of interest 420, such as a prostate. Each 2D slice may have a finite thickness T. The distance between two adjacent slices may be L. The plurality of 2D slices that define the 3D volume 410 may be represented by their 2D projection on the front surface (e.g., a surface perpendicular to plane 400) of volume 410. The 2D projection is denoted as projection 411. As shown in FIG. 4, projection 411 may represent the thickness T, distance L, and any particular slice (e.g., slice 418 denoted by four small arrows can be represented by a shadowed block in projection 411).

The plurality of 2D slices may define a plurality of spatial locations relative to anatomical region of interest 420. For example, the 2D slices may indicate spatial locations of a plurality of 2D images to be acquired by image acquisition device 140 during a radiotherapy session. The thickness of a slice may indicate the resolution of the 2D images along a direction perpendicular to the primary plane of motion (e.g., when the primary plane of motion is the sagittal plane, the direction perpendicular to the sagittal plane is the left/right direction). During the course of image acquisition, images corresponding to the 2D slices may be acquired (e.g., acquiring images at the spatial locations defined by the slices). These images may be used to determine a motion of anatomical region of interest 420 during the radiotherapy session.

Figure 5:
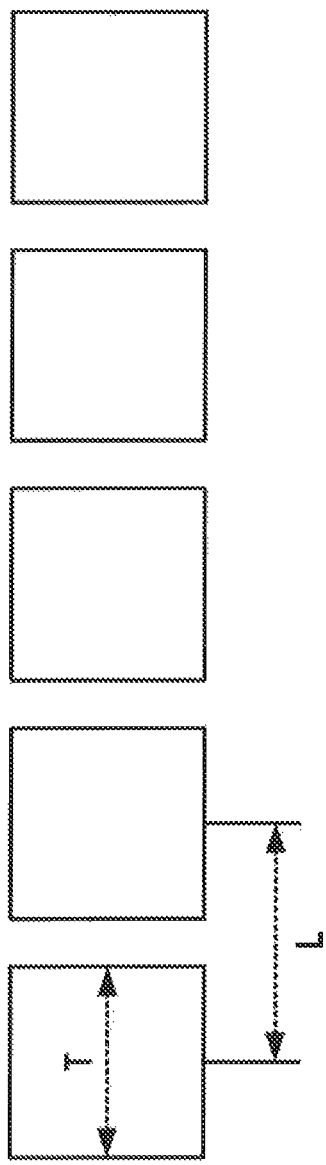
FIG. 5 illustrates another set of exemplary 2D slices, according to some embodiments of the present disclosure.

In FIG. 4, the distance L between two adjacent slices (e.g., measured between the centers of the two slices) is the same as thickness T, indicating that the two slices (e.g., 412 and 416) are right next to each other without a gap in between. This arrangement has an advantage that the plurality of slices can cover the entire 3D volume 410. However, leaving no gap between adjacent slices, when coupled with sequential sweeping, may lead to a "bleeding" effect, in which excited tissue in a previous slice may not have sufficient time to relax to equilibrium before acquisition starts in the next, adjacent slice. Therefore, the next, adjacent slice may be affected by the insufficient relaxation of the previous slice. The bleeding effect may be alleviated by leaving a gap between two adjacent slices. In addition, leaving a gap between two adjacent slices may also improve acquisition speed. FIG. 5 shows an exemplary arrangement of five slices. The distance between two adjacent slices L is greater than the thickness T of each slice. As a result, a small gap is formed between adjacent slices.

Figure 6A:
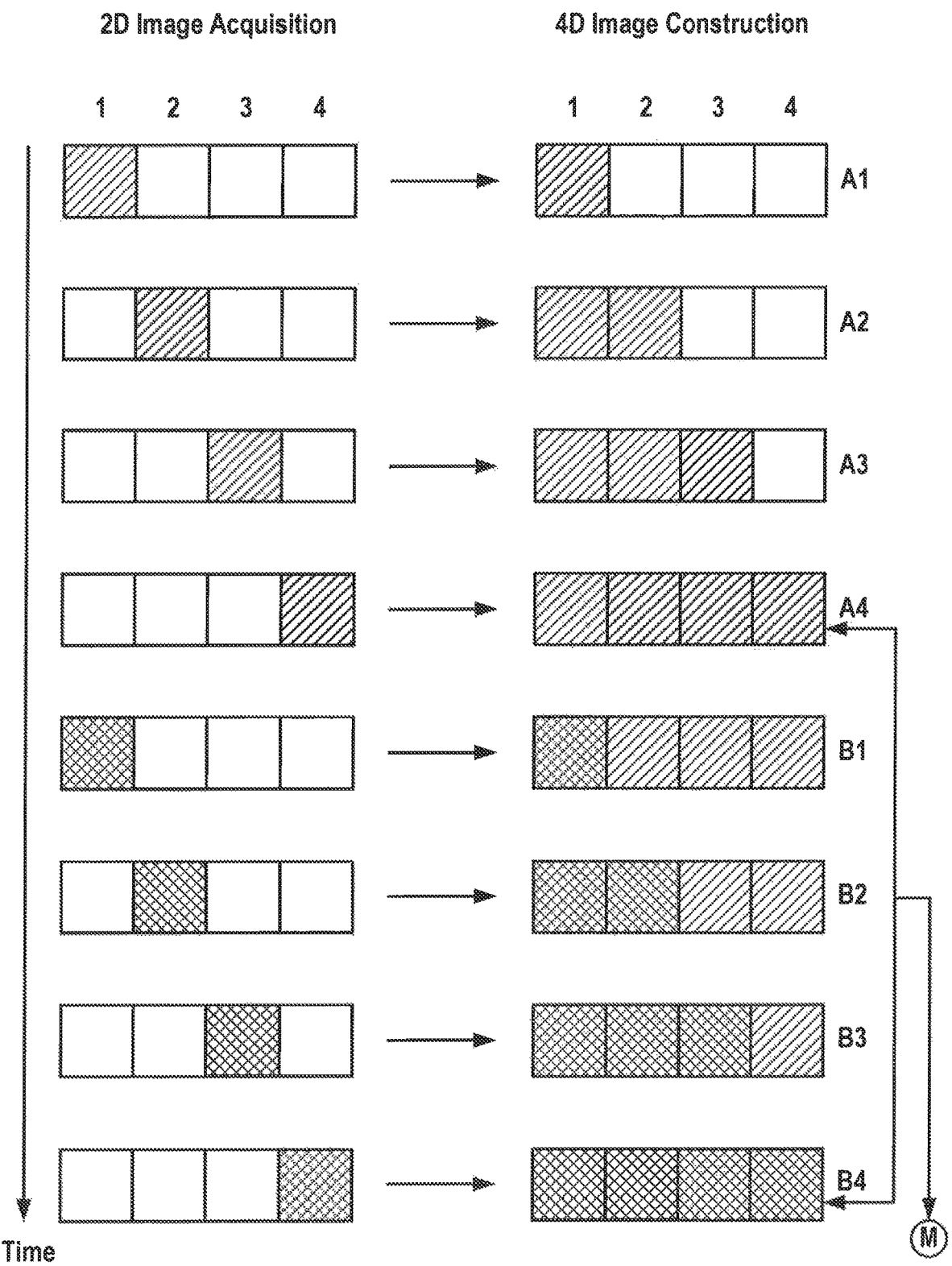
FIG. 6A illustrates an exemplary process of constructing a 4D image and an exemplary process of determining a motion based on the 4D image, according to some embodiments of the present disclosure.

FIG. 6A illustrates an exemplary process of constructing a 4D image and an exemplary process of determining a motion based on the 4D image, according to some embodiments of the present disclosure. In FIG. 6A, the left column indicates images acquired by image acquisition device 140 over time, and the right column indicates a 4D image (3D plus time, also referred to as a 3D cine image) constructed based on the acquired images. The example shown in FIG. 6A uses the same slice arrangement as in FIG. 4, but uses numbers 1, 2, 3, 4 to indicate slices 412, 414, 416, and 418, for simplicity. During image acquisition, control console 110 may control image acquisition device 140 to sequentially (e.g., one image at a time) acquire a series of 2D images, each corresponding to one of the slices. In some embodiments, control console 110 may control image acquisition device 140 to sweep (e.g., one after another or one by one) across the slices. For example, as shown in FIG. 6A, at the first time point A1, image acquisition device 140 may acquire a 2D image corresponding to slice 1, as indicated by the shadowed box in the first row of the left column. The 2D image corresponds to slice 1 when the 2D image shows anatomical structures at the same location as defined by slice 1. The acquired 2D image may then be stored at slot 1, correspond to slice 1, of the 4D image.

At time point A2, control console 110 may control image acquisition device 140 to acquire another 2D image, this time corresponding to slice 2. The acquired 2D image may then be stored at slot 2, corresponding to slice 2, of the 4D image. Similarly, at time points A3 and A4, 2D images corresponding to slices 3 and 4, respectively, may be acquired and stored at slots 3 and 4, respectively.

After all 4 slots of the 4D image are filled, a snapshot of the 4D image may be obtained. As used herein, a snapshot of a 4D image refers to a 3D volumetric image consisting of a plurality of 2D images at a particular time point. On the other hand, a 4D image may be seen as a time evolving 3D volumetric image including a series of snapshots. The 3D volumetric image or snapshot may be defined by the plurality of 2D slices such as the slices shown in FIG. 4. In other words, the snapshot may include a plurality of slots that are arranged in the same manner as the slices, and covers substantially the same 3D space as volume 410. Each slot may be filled with 2D images acquired by image acquisition device 140 at the spatial location defined by a corresponding slice. In some embodiments, the acquisition of a 2D image may be in real time or close to real time. For example, the acquisition time of a 2D image may be less than 200 milliseconds.

In some embodiment, once an initial snapshot is obtain (e.g., at time point A4), the 4D image may continue involving over time. This may be achieved by repeatedly sweeping across the 2D slices and updating the corresponding slot of the 4D image as new data arrive. Referring to FIG. 6A for example, at time point B1, image acquisition device 140 may acquire a new 2D image (indicated by a cross-line shadowed box) corresponding to slice 1 (e.g., in a new sweep). The new 2D image may be stored at or inserted into slot 1 of the 4D image, replacing the previously acquired 2D image. Similarly, at time points B2, B3, and B4, new 2D images corresponding to slices 2, 3, and 4 may be acquired and inserted into slots 2, 3, and 4, respectively, replacing their respective old data.

When new data replace old data in any slot, the 4D image is refreshed. The 4D image is fully refreshed when all slots have been updated with new data. A refresh time refers to a time duration it takes to refresh the 4D image. For a single slot refresh, the refresh time may be close to the acquisition time of a 2D image. For a full refresh, the refresh time may depend on the acquisition time of an individual 2D image and the number of slots contained within the 4D image.

In FIG. 6A, the snapshot at B4 fully refreshes the snapshot at A4. If a motion of the anatomical region of interest occurs during the time period B4-A4, then the motion may be captured by the snapshot at B4. Control console 110 may determine the motion (indicated by an M in a circle) by comparing the snapshot at B4 with the snapshot at A4. If the comparison yields any difference in position, size, or shape of the anatomical region of interest, it may indicate that the motion occurs. Various methods may be used to compare the 3D snapshots, including 3D rigid or deformable registration, 3D segmentation of one or more anatomical structures, etc.

Comparison of two snapshots where one fully refreshes the other may be suitable for capturing relatively slow motions, such as prostate motions due to relaxation or bladder filling. For faster motions, such as prostate motions due to gas or coughing, control console 110 may compare two snapshots where one only partially refreshes the other (e.g., comparing snapshot at B2 with snapshot at A4).

Figure 6B:
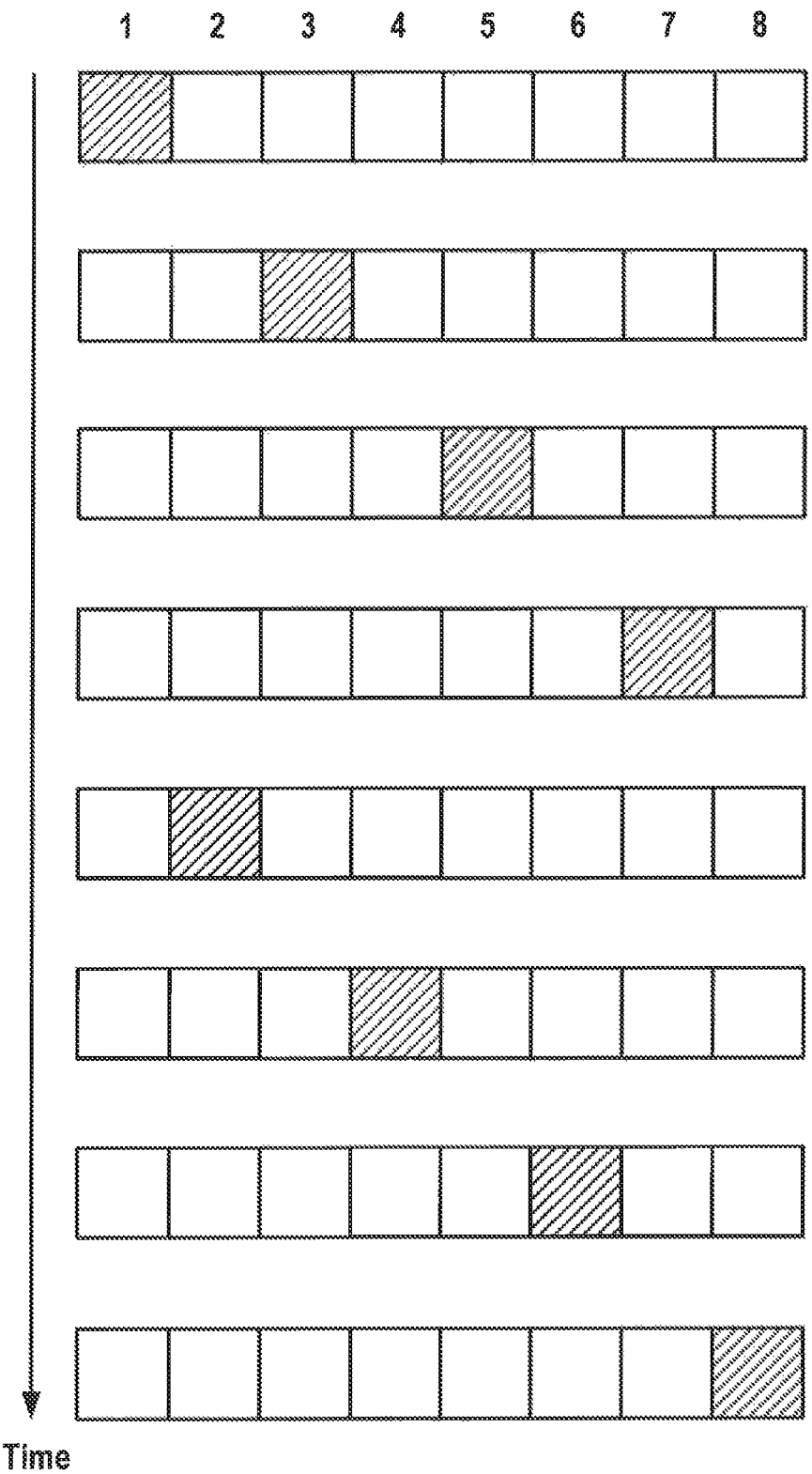
FIG. 6B illustrates an exemplary image acquisition process to reduce "bleeding" effect, according to some embodiments of the present disclosure.

As described above, sequentially acquiring 2D images, such as the method shown in FIG. 6A, may lead to bleeding effect in which a previous neighboring slice may still be partially excited and therefore bleed into the next slice. In some embodiments, the bleeding effect may not be significant and sequential acquisition may be used. In other embodiments, non-sequential acquisition may be used to reduce or eliminate the bleeding effect. For example, FIG. 6B shows an exemplary 2D image acquisition method to reduce to bleeding effect. In FIG. 6B, a volume including 8 slices is used to illustrate the acquisition sequence. To reduce the bleeding effect between neighboring slices, the 2D images may be acquired every other slice. For example, FIG. 6B shows an example in which slices 1, 3, 5, and 7 are acquired one after another, then slices 2, 4, 6, and 8 are acquired one after another. Because there is a spatial gap (e.g., one slice) between successively acquired slices, the bleeding effect can be reduced or even prevented. While FIG. 6B shows only one example of non-sequential acquisition, any suitable or similar acquisition method may be used. For example, instead of acquiring odd numbered slices first followed by the even numbered slices, even numbered slices can be acquired before odd numbered slices. In another example, the gap between successively acquired slices may include one, two, or more slices. In some embodiment, the slices may be acquired in a random order. As used herein, traversing all 2D slices in the volume, either sequentially or non-sequentially, is referred to as a sweep. Therefore, sweeping across the 2D slices includes both sequentially sweeping and non-sequentially sweeping.

Once the 2D images are acquired in a non-sequential manner, they can be inserted into corresponding slots contained within the 4D image, similar to the method described above in connection with FIG. 6A.

Figure 7:
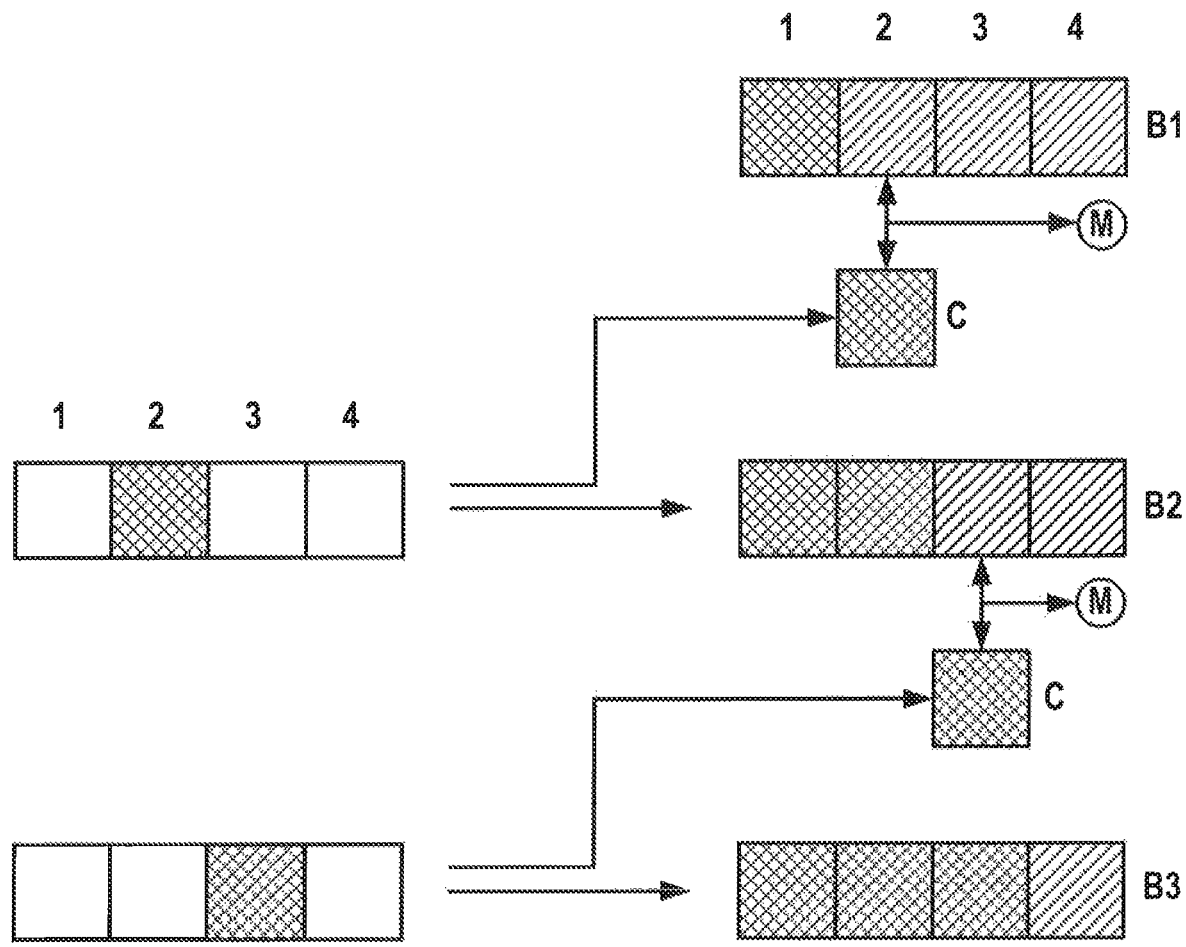
FIG. 7 illustrates an exemplary process of determining a motion based on comparison of 2D images, according to some embodiments of the present disclosure.

In some applications, 2D images may also be processed separately in a parallel stream to capture fast motions. FIG. 7 illustrates an exemplary implementation of such a process. FIG. 7 shows part of FIG. 6A plus a buffering and comparing parallel stream. For example, at time point B2, an image corresponding to slice 2 is acquired and inserted into the 4D image at slot 2, the same as in FIG. 6A. In addition, the image can be stored in a buffer C, indicating a currently acquired image. The current acquired image can be compared with an older 2D image (e.g., the last acquired 2D image) corresponding to the same slice. For example, the image stored in buffer C can be compared with the image stored in slot 2 of the 4D image at time point B1. The comparison result may indicate whether motion occurs during the time period from B1 to B2. Similarly, at time point B3, the currently acquired image, an image corresponding to slice 3, may be acquired, stored in buffer C, and compared with the image stored in slot 3 of the 4D image at time point B2. The process shown in FIG. 7 tracks motion based on partially refreshed 4D image and may be used to capture fast motions. In some embodiments, this method may be used in conjunction with the method shown in FIG. 6A, which tracks motion based on fully refreshed 4D image.

Once a motion is detected, control console 110 may perform various operations to compensate for the motion. For example, control console 110 may control radiotherapy device 130 to gate a radiation beam if a certain motion exceeds a threshold. In another example, control console 110 may modify the configuration of a multi-leaf collimator (MLC) to change the beam shape. In another example, control console 110 may move patient support system 210 to realign the anatomical region of interest with the isocenter of radiation beam 230. Other operation or treatment parameters may also be changed.

Figure 8:
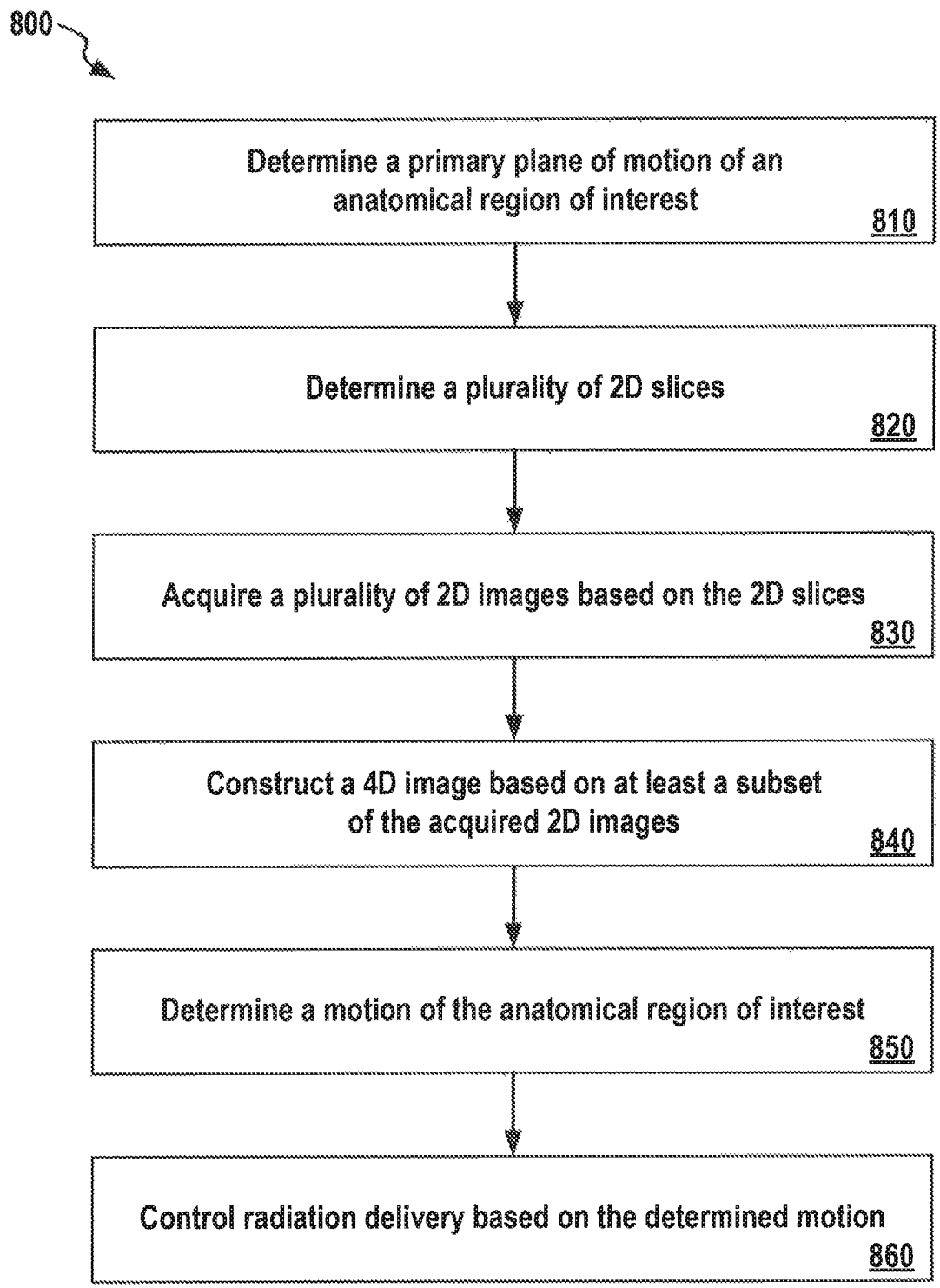
FIG. 8 is a flowchart of an exemplary method of managing motions of an anatomical region of interest of a patient during an image-guided radiotherapy session, according to some embodiments of the present disclosure.

FIG. 8 is a flowchart of an exemplary method 800 of managing motions of an anatomical region of interest of a patient during an image-guided radiotherapy session, according to some embodiments of the present disclosure. Method 800 includes a plurality of steps, some of which may be optional.

In step 810, control console 110 may determine a primary plane of motion (e.g., plane 400) of an anatomical region of interest (e.g., 420). In some embodiments, the primary plane of motion may be determined based on the type of anatomical region of interest. For example, for prostate treatment, sagittal plane may be determined as the primary plane of motion for different patients. In some embodiments, the primary plane of motion may be patient dependent. For example, for liver treatment, the primary plane of motion may be determined based on analysis of medical images of the patient.

At step 820, control console 110 may determine a plurality of 2D slices (e.g., slices 412, 414, 416, and 418) parallel to the primary plane. The 2D slices may define a 3D volume (e.g., 410) that substantially encloses the anatomical region of interest (e.g., 420). The 2D slices may define a plurality of spatial locations relative to the anatomical region of interest. For example, the 2D slices may define the locations in which images to be acquired by image acquisition device 140 during a radiotherapy session.

At step 830, control console 110 may control image acquisition device 140 to acquire a plurality of 2D images based on the slices. For example, as shown in FIG. 6A, the images may be acquired sequentially from one slice to another. In another example, as shown in FIG. 6B, the images may be acquired in a non-sequential manner. After all slices have been swept (either sequentially or non-sequentially), image acquisition device 140 may repeat the sweeping to continuously acquire images slice by slice. In some embodiment, when sequential sweeping is used, the sweeping may be always from slice 1 to slice N (when there are N slices in total). This manner of sweeping may be referred to as a forward sequential sweeping. In some embodiments, the sequential sweeping may be always from slice N to slice 1—a backward sequential sweeping. In some embodiments, the sequential sweeping may be back and forth (e.g., from 1 to N then back to 1, etc.). Other sweeping manners, such as non-sequential sweepings (e.g., odd-then-even, even-then-odd, random, etc.) may also be used.

At step 840, control console 110 may construct a 4D image based on at least a subset of the acquired 2D images. For example, as shown in FIG. 6A, the 4D image may be constructed by receiving the 2D image and inserting it into the corresponding slot. If old image data exist at a particular slot, the old data may be replaced by new data. The 3D image may evolve over time as new 2D images are acquired and inserted.

At step 850, control console 110 may determine a motion of the anatomical region of interest based on a comparison between 3D snapshots of the 4D image at different times. For example, the comparison may be performed based on fully refreshed 4D image (e.g., FIG. 6A) or partially refreshed 4D image (e.g., FIG. 7). The motion of the anatomical region of interest may include changes in position, size, or shape.

As step 860, control console 110 may control radiation delivery based on the determined motion. For example, various operation and/or treatment parameters may be changed to compensate for the motion, including controlling a gating of a radiation beam, a modification of a MLC, a movement of patient supporting system 210, etc.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

Embodiments may be implemented with computer-executable instructions. The computer-executable instructions may be organized into one or more computer-executable components or modules. Embodiments may be implemented with any number and organization of such components or modules. For example, aspects of the disclosure are not limited to the specific computer-executable instructions or the specific components or modules illustrated in the figures and described herein. Other embodiments may include different computer-executable instructions or components having more or less functionality than illustrated and described herein.

When introducing elements of aspects of the disclosure or the embodiments thereof, the articles "a," "an," and "the" are intended to mean that there are one or more of the elements. The terms "comprising," "including," and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. A radiotherapy system, comprising:
   an image acquisition device configured to acquire images of an anatomical region of interest of a patient;
   a radiotherapy device configured to deliver a dose of radiation to the anatomical region of interest based on the images of the anatomical region of interest;

a processor device configured to:
 determine a primary plane of motion of the anatomical region of interest;
 determine a plurality of two-dimensional (2D) slices parallel to the primary plane, the plurality of 2D slices defining a three-dimensional (3D) volume substantially enclosing the anatomical region of interest;
 control the image acquisition device to acquire a plurality of 2D images based on the plurality of 2D slices;
 determine a motion of the anatomical region of interest based on at least a subset of the acquired plurality of 2D images; and
 control radiation delivery based on the determined motion.

2. The radiotherapy system of claim 1, wherein the image acquisition device is configured to acquire 2D Magnetic Resonance Imaging (MRI) images of the anatomical region of interest of the patient.

3. The radiotherapy system of claim 1, wherein the radiotherapy device includes a linear accelerator (LINAC).

4. The radiotherapy system of claim 1, wherein the anatomical region of interest includes a prostate, a cervix, a uterus, a rectum, a bladder, a penile bulb, a lumpectomy cavity in a breast, a tumor, or a node of the patient.

5. The radiotherapy system of claim 1, wherein the primary plane of motion is patient dependent.

6. The radiotherapy system of claim 1, wherein the primary plane of motion includes a sagittal plane, a coronal plane, or a transverse plane.

7. The radiotherapy system of claim 1, wherein the plurality of 2D slices define a plurality of spatial locations relative to the anatomical region of interest.

8. The radiotherapy system of claim 1, wherein the processor device is configured to control the image acquisition device to acquire a series of 2D images, each corresponding to one of the plurality of 2D slices.

9. The radiotherapy system of claim 8, wherein the processor is configured to control the image acquisition device to acquire the series of 2D images by sweeping across the plurality of 2D slices.

10. The radiotherapy system of claim 9, wherein the processor is configured to control the image acquisition device to acquire the series of 2D images by repeatedly sweeping across the plurality of 2D slices.

11. The radiotherapy system of claim 10, wherein the processor device is configured to determine the motion of the anatomical region of interest by comparing a first 2D image within the series that corresponds to a first 2D slice with a second 2D image within the series that also corresponds to the first 2D slice, wherein the first and second 2D images are acquired at different times.

12. The radiotherapy system of claim 10, wherein the processor device is configured to construct a four-dimensional (4D) image of the 3D volume based on at least a subset of the series of 2D images.

13. The radiotherapy system of claim 12, wherein the processor device is configured to:
 receive a first 2D image within the series that corresponds to a first 2D slice;
 insert the first 2D image into the 4D image;
 receive a second 2D image within the series that also corresponds to the first 2D slice; and
 replace the first 2D image in the 4D image with the second 2D image.

14. The radiotherapy system of claim 12, wherein the processor device is configured to determine the motion of the anatomical region of interest by comparing 3D snapshots of the 4D image at different times.

15. The radiotherapy system of claim 1, wherein the motion of the anatomical region of interest includes at least one of position change or deformation.

16. The radiotherapy system of claim 1, wherein the processor device is configured to determine the motion and control the radiation delivery during a radiotherapy session.

17. The radiotherapy system of claim 1, wherein the processor is configured to control at least one of the following based on the determined motion:
 a gating of a radiation beam;
 a modification of a multi-leaf collimator (MLC); or
 a movement of a patient supporting system.

18. A method for managing motions of an anatomical region of interest of a patient during an image-guided radiotherapy session, implemented by a processor device of a radiotherapy system, comprising:
 determining a primary plane of motion of the anatomical region of interest;
 determining a plurality of two-dimensional (2D) slices parallel to the primary plane, the plurality of 2D slices defining a three-dimensional (3D) volume substantially enclosing the anatomical region of interest;
 controlling an image acquisition device to acquire a plurality of 2D images based on the plurality of 2D slices;
 determining a motion of the anatomical region of interest based on at least a subset of the acquired plurality of 2D images; and
 controlling a radiotherapy device to deliver radiation based on the determined motion.

19. The method of claim 18, wherein the image acquisition device includes a Magnetic Resonance Imaging (MRI) machine for acquiring 2D MRI images of the anatomical region of interest of the patient.

20. The method of claim 18, wherein the radiotherapy device includes a linear accelerator (LINAC).

21. The method of claim 18, wherein the anatomical region of interest includes a prostate, a cervix, a uterus, a rectum, a bladder, a penile bulb, a lumpectomy cavity in a breast, a tumor, or a node of the patient.

22. The method of claim 18, wherein the primary plane of motion is patient dependent.

23. The method of claim 18, wherein the primary plane of motion includes a sagittal plane, a coronal plane, or a transverse plane.

24. The method of claim 18, wherein the plurality of 2D slices define a plurality of spatial locations relative to the anatomical region of interest.

25. The method of claim 18, comprising:
 controlling the image acquisition device to acquire a series of 2D images, each corresponding to one of the plurality of 2D slices.

26. The method of claim 25, comprising:
 controlling the image acquisition device to acquire the series of 2D images by sweeping across the plurality of 2D slices.

27. The method of claim 26, comprising:
 controlling the image acquisition device to acquire the series of 2D images by repeatedly sweeping across the plurality of 2D slices.

28. The method of claim 27, wherein determining the motion of the anatomical region of interest includes:

comparing a first 2D image within the series that corresponds to a first 2D slice with a second 2D image within the series that also corresponds to the first 2D slice, wherein the first and second 2D images are acquired at different times.

29. The method of claim 27, comprising:
constructing a four-dimensional (4D) image of the 3D volume based on at least a subset of the series of 2D images.

30. The method of claim 29, wherein constructing the 4D image includes:
receiving a first 2D image within the series that corresponds to a first 2D slice;
inserting the first 2D image into the 4D image;
receiving a second 2D image within the series that also corresponds to the first 2D slice; and
replacing the first 2D image in the 4D image with the second 2D image.

31. The method of claim 29, wherein determining the motion of the anatomical region of interest includes:
comparing 3D snapshots of the 4D image at different times.

32. The method of claim 18, wherein the motion of the anatomical region of interest includes at least one of position change or deformation.

33. The method of claim 18, wherein controlling the radiotherapy device to deliver radiation based on the determined motion includes at least one of:
controlling a gating a radiation beam;
controlling a modification of a multi-leaf collimator (MLC); or
controlling a movement of a patient supporting system.

34. A radiotherapy system, comprising:
an image acquisition device configured to acquire Magnetic Resonance Imaging (MRI) images of an anatomical region of interest of a patient;
a radiotherapy device including a linear accelerator (LINAC) and configured to deliver a dose of radiation to the anatomical region of interest based on the images of the anatomical region of interest;
a processor device configured to:
determine a primary plane of motion of the anatomical region of interest, the primary plane of motion including a sagittal plane, a coronal plane, or a transverse plane;
determine a plurality of two-dimensional (2D) slices parallel to the primary plane, the plurality of 2D slices defining:
a three-dimensional (3D) volume substantially enclosing the anatomical region of interest; and
a plurality of spatial locations relative to the anatomical region of interest;
control the image acquisition device to acquire a series of 2D images by repeatedly sweeping across the plurality of 2D slices, wherein each 2D image within the series corresponds to one of the plurality of 2D slices;
construct a four-dimensional (4D) image of the 3D volume based on at least a subset of the series of 2D images, including:
receive a first 2D image within the series that corresponds to a first 2D slice;
insert the first 2D image into the 4D image;
receive a second 2D image within the series that also corresponds to the first 2D slice; and
replace the first 2D image in the 4D image with the second 2D image;
determine a motion of the anatomical region of interest based on a comparison between 3D snapshots of the 4D image at different times during a radiotherapy session, wherein the motion of the anatomical region of interest includes at least one of position change or deformation; and
control radiation delivery based on the determined motion, including at least one of:
control a gating of a radiation beam;
control a modification of a multi-leaf collimator (MLC); or
control a movement of a patient supporting system.

* * * * *